United States Patent [19]
Adair et al.

[11] Patent Number: 6,040,298
[45] Date of Patent: Mar. 21, 2000

[54] METHODS FOR TREATMENT WITH COMPOSITIONS EFFECTIVE AGAINST ACYCLOVIR-RESISTANT STRAINS OF HERPES VIRUSES

[75] Inventors: Dennis W. Adair, Suisun, Calif.; Karl M. Johnson, Bozeman, Mont.; Earl R. Kern, Birmingham, Ala.

[73] Assignee: Oclassen Pharmaceuticals, Inc., San Rafael, Calif.

[21] Appl. No.: 07/995,843

[22] Filed: Dec. 23, 1992

[51] Int. Cl.⁷ .............................. A61K 31/70; C07H 17/00
[52] U.S. Cl. .............................. 514/50; 514/49; 536/28.3; 536/28.52; 536/28.53; 536/28.54; 536/28.55
[58] Field of Search .............................. 536/28.3, 28.53, 536/28.52, 28.54, 28.55; 514/49, 50

[56] References Cited

U.S. PATENT DOCUMENTS

| | | | |
|---|---|---|---|
| 4,211,773 | 7/1980 | Lopez et al. | 514/49 |
| 4,489,052 | 12/1984 | Price | 424/1.73 |
| 4,594,339 | 6/1986 | Lopez et al. | 514/42 |
| 4,666,892 | 5/1987 | Fox et al. | 514/49 |
| 5,010,060 | 4/1991 | Laubert et al. | 514/49 |

*Primary Examiner*—David Guzo
*Attorney, Agent, or Firm*—Pennie & Edmonds LLP

[57] ABSTRACT

The present invention relates to pharmaceutical compositions useful for the treatment of subjects suffering from an infection or disease caused by herpes virus strains that are resistant to treatment with acyclovir. In particular, it has been discovered that the low dosage amounts of 1-(2'-deoxy-2'-fluoro-β-D-arabinofuranosyl)-5-iodouracil (FIAU) are effective in inhibiting replication of acyclovir-resistant HSV strains. The present invention is also directed to methods of the preparation of pharmaceutical antiviral compositions and to the methods of their use in the treatment of infection or disease.

27 Claims, 2 Drawing Sheets

METHODS FOR TREATMENT WITH COMPOSITIONS EFFECTIVE AGAINST ACYCLOVIR-RESISTANT STRAINS OF HERPES VIRUSES

1. FIELD OF THE INVENTION

The present invention relates to pharmaceutical compositions useful for the treatment of human subjects suffering from an infection or disease caused by Herpes viruses (HSV). In particular, human subjects who suffer from infections caused by strains of HSV which are resistant to acyclovir treatment can benefit from a therapeutic regimen that includes the administration of the compositions of the present invention.

2. BACKGROUND OF THE INVENTION

The nucleoside compound 1-(2'-deoxy-2'-fluoro-β-D-arabinofuranosyl)-5-iodouracil (FIAU) has been described, for example, in U.S. Pat. No. 4,211,773, as an antiviral and an antitumor agent. The disclosure of this patent reference includes methods for the preparation of the compound FIAU and also claims pharmaceutical compositions comprising a general class of pyrimidine analogs, including FIAU, 1-(2'-deoxy-2'-fluoro-β-D-arabinofuranosyl)-5-iodocytosine (FIAC) or pharmaceutically acceptable acid addition salts thereof. Cell culture data showing the inhibition of Herpes Simplex Virus (HSV) replication are presented for a variety of nucleoside analogs. In the case of FIAC, in vivo data in mice inoculated with HSV-1 are also presented, showing improved survival rates for those test animals that received FIAC compared with control animals.

Other studies involving the in vitro activity of FIAC and its primary deaminated uracil metabolite, FIAU, against several herpes group viruses, particularly herpes simplex (HSV) types 1 and 2, varicella zoster (VZV), and cytomegalovirus (CMV) have been performed. Although not elucidated in definitive detail, FIAC/FIAU (FIAC can be considered the prodrug of FIAU) apparently exert their effect by serving as substrates for viral DNA polymerase. (Cheng, Y.-C. et al. Antimicrobial Agents and Chemotherapy 1981, 20:420–423.) The in vitro $ED_{90}$ value for FIAC/FIAU against these viruses ranges from approximately 0.05 $\mu$M for HSV-1 to about 0.5 $\mu$M for CMV. Typical cellular toxicity concentrations ($ID_{50}$) are approximately in the 10 $\mu$M range. (Lopez, C. et al. Antimicrobial Agents and Chemotherapy 1980, 17(5):803–806; Schinazi, R. F. et al. Antimicrobial Agents and Chemotherapy 1986, 29:77–84; Colacino, J. M. et al. Antimicrobial Agents and Chemotherapy 1983, 24:505–508; Hantz, O. et al. Antiviral Research 1984, 4:187–189).

2.1. Previous Clinical Studies

In studies designed to determine the effectiveness of FIAC against herpes group viruses, involving more than 100 patients, including immune-compromised patients, FIAC was found to be nearly completely absorbed following oral administration and was very rapidly converted to FIAU. The half-life of FIAU was sufficiently long to allow for effective antiviral concentrations >0.2 $\mu$M to be present in the plasma for 8 to 12 hours after an oral dose of FIAC of ≦2.5 mg/kg that was not acutely toxic. (Feinberg, A. et al. Antimicrobial Agents and Chemotherapy 1985, 27:733–738.) Due to the severe nature of disease in these very debilitated patients, high doses (~10–20 mg/kg-day) of FIAC were used and it proved very difficult and often impossible to distinguish drug toxicity from the natural course of these extremely ill patients.

These studies showed that the active anti-herpetic compound in the plasma is FIAU. Oral FIAC, 1 mg/kg/day, was almost never detected in blood two hours after dosing, verifying its rapid deamination to FIAU. FIAC 1 mg/kg/day given in 3 divided doses resulted in FIAU average peak levels of approximately 0.5 $\mu$g/ml, were consistent between patients, and stable from Day 3 of dosing onward. The trough values had the same characteristics, except that they averaged approximately 0.05 $\mu$g/ml. Values of FAU were low, dose dependent (~0.05 $\mu$g/ml at 0.6 mg/kg-day vs ~0.10 $\mu$g/ml at 1.0 mg/kg-day) and did not increase with continued dosing. These results confirmed that FIAU is the predominant active compound present in the plasma, and that neither FIAC, FIAU, nor their metabolites accumulated in the plasma during month long TID dosing.

FIAU is the primary metabolite of FIAC and the administration of the metabolite simplifies the metabolism involved by eliminating the direct conversion of FIAC to FAC, a potentially more toxic metabolite. (Philips, F. S. et al. Cancer Research 1983, 43:3619–3627.)

2.2. Acyclovir Treatment for HSV

Despite the foregoing clinical trials, acycloguanosine, i.e., acyclovir (ACV), remains the principal approved treatment for mucocutaneous HSV infection. Acyclovir, 9-(2-hydroxyethoxymethyl) guanine, is a guanine derivative with an acyclic chain. It requires the herpes virus-specified enzyme, deoxythymidine-deoxycytidine kinase (thymidine kinase) to phosphorylate it intracellularly, so that the compound is "activated." The "activated" compound inhibits the herpes virus-specified DNA polymerase at least 10 times more effectively than cellular DNA polymerase. It acts as both inhibitor and substrate for the viral polymerase competing with GTP for incorporation into DNA, leading to chain termination because ACV lacks the 3'-hydroxyl group required for chain elongation. Since activation of ACV requires the herpes virus thymidine kinase, the drug is essentially nontoxic to uninfected cells but powerfully inhibitory to viral DNA synthesis in infected cells.

In cell culture, herpes simplex viruses types 1 and 2 (HSV-1 and HSV-2) are very susceptible to ACV. Varicella-zoster virus (VZV) is susceptible at somewhat higher concentrations of the drug. The other human herpes viruses, EBV (Epstein Bar virus) and CMV (cytomyalovirus), neither of which is known to possess a gene coding for thymidine kinase, are nevertheless susceptible to acyclovir, albeit at much greater concentrations. In man, acyclovir is given intravenously, orally or topically and displays activity against herpes simplex viruses type-1 and type-2, and varicella-zoster. For example, acyclovir is very effective against herpes simplex keratitis. Intravenous acyclovir protects transplant recipients against reactivation of their latent herpes simplex. Acyclovir cream has been reported to shorten the healing time of recurrent herpes labialis. Whether delivered topically, orally, or intravenously, acyclovir reduces the duration of virus shedding, local pain/itching, and lesion healing time in primary herpes genitalis, though less persuasively in the more short-lived recurrent attacks, particularly in immunocompromised patients.

Despite ACV's efficacy in treating the foregoing conditions, most clinical studies have revealed no effect against CMV (congenital CMID of infants, or CMV pneumonia following bone marrow transplantation), nor against EBV.

Because of its proven efficacy and relative lack of toxicity, acyclovir has been considered the drug of choice for treating herpes virus infections. However, acyclovir-resistant mutants have emerged. In culture, the mutations have been located in either the gene coding for the viral thymidine-kinase (TK) or that for DNA polymerase. There appear to be two kinds of TK mutants: those failing to produce appreciable levels of TK, and those in which an altered TK enzyme is produced in substantial amounts, i.e., a TK enzyme that has an altered substrate specificity so that it can no longer satisfactorily phosphorylate acyclovir. Acyclovir resistant mutants have been isolated from man following acyclovir therapy.

3. SUMMARY OF THE INVENTION

Figure 1:
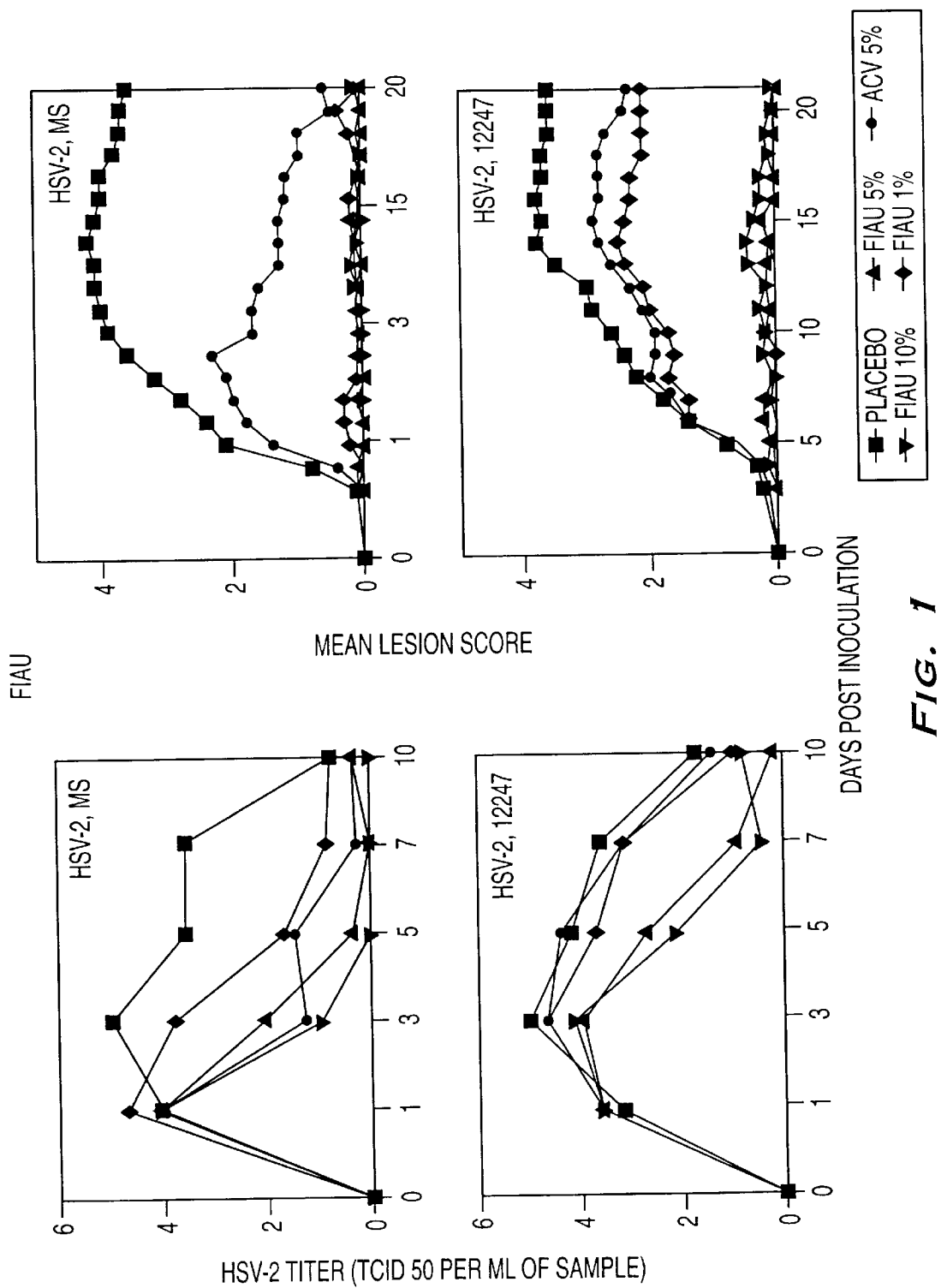
FIG. 1. The four panels of FIG. 1 show the inhibition of ACV-resistant and ACV-sensitive strains of HSV by FIAU.

To the great surprise of the applicants, pharmaceutical compositions comprising 1-(2'-deoxy-2'-fluoro-β-D-arabinofuranosyl)-5-iodouracil (FIAU, also known as fialuridine) and a pharmaceutically acceptable carrier have been discovered which are effective at inhibiting replication of HSV strains that are resistant to treatment with acyclovir. In accordance with the invention, such pharmaceutical formulations of FIAU or its prodrug, FIAC, may be utilized to treat herpes virus infections in human patients. A number of groups of herpes viruses may be treated in accordance with the invention, including but not limited to HSV-1, HSV-2, VZV and CMV.

Thus, it is an objective of the present invention to provide a pharmaceutical composition for the treatment of infection or disease caused by acyclovir-resistant HSV which comprises a pharmaceutically acceptable carrier and an amount of FIAU sufficient to provide an antivirally effective dosage of FIAU in the range of about 0.05 to about 10 mg/kg-day. Preferably, the amount of FIAU provided falls in the range of about 0.5 to about 5 mg/kg-day. The present invention also contemplates a pharmaceutical composition comprising a compound that is a prodrug of FIAU or a compound that is a metabolite of FIAU. In particular, FIAC can be used as a prodrug, in place of FIAU. Likewise, a metabolite of FIAU, 1-(2'-deoxy-2'-fluoro-β-D-arabinofuranosyl)uracil (FAU), can be used to form at least part of the active ingredient of the pharmaceutical antiviral composition of the present invention. Yet other members of the general class of deoxyfluorinated pyrimidine nucleosides can also be used to form at least part of the active ingredient, including 1-(2'-deoxy-2'-fluoro-β-D-arabinofuranosyl)-5-methyluracil (FMAU) and 1-(2'-deoxy-2'-fluoro-β-D-arabinofuranosyl)-5-ethyluracil (FEAU).

Yet another objective of the present invention is to provide a pharmaceutical composition for the topical treatment of infection or disease caused by acyclovir-resistant HSV which comprises a concentration of FIAU, a compound that is a prodrug of FIAU or a compound that is a metabolite of FIAU which concentration if tested in an in vitro plaque reduction assay is equivalent to 20 percent or greater of the concentration of FIAU, its prodrug or metabolite (in μg/ml) required to reduce the plaque formation induced by said herpes virus strain by fifty percent ($EC_{50}$) and a pharmaceutically acceptable carrier.

In yet another aspect of the present invention, pharmaceutical compositions for the topical treatment of infection or disease caused by ACV-resistant HSV are disclosed which comprise FIAU, a compound that is a prodrug of FIAU or a compound that is a metabolite of FIAU and a pharmaceutically acceptable carrier, said topical compositions containing about 0.1–25% by weight of FIAU, its prodrug or metabolite.

Further objects of the invention include providing compositions effective in a therapeutic regimen against ACV-resistant HSV while minimizing or eliminating the side effects associated with the administration of FIAU, its prodrug or metabolite, especially at the high dosages recommended in the prior art.

Also contemplated by the present applicants are methods for the preparation of pharmaceutical antiviral compositions comprising admixing the antivirally active ingredients with a pharmaceutically acceptable carrier. In particular, pharmaceutical compositions in the form of solutions, suspensions, syrups, tablets, caplets or capsules are contemplated which are suitable for topical, oral or parenteral administration. Methods of treating human patients infected with ACV-resistant HSV or suffering from a disease caused by ACV-resistant HSV comprising the administration of the compositions of the present invention are likewise contemplated. Modes of administration include topical, oral or parenteral administration. Further, the period of treatment is variable, generally lasting about 3 to about 30 days, preferably about 7–21 days.

Thus, these and other objects of the present invention will become apparent to those skilled in the art from a reading of the instant disclosure.

4. DETAILED DESCRIPTION OF THE INVENTION

4.1. Antiviral Formulations

Use of pharmaceutically acceptable carriers to formulate FIAC and FIAU into dosages suitable for topical or systemic administration is contemplated. Topical preparations consisting of solutions, creams, ointments, or gels may be utilized. Pharmaceutical preparations for the treatment of vaginal infections, such as suppositories, creams, or foams may be prepared. Ophthalmic infection, i.e., herpes keratitis, may be treated with normal dosage release of FIAU, such as drops or ointments, or by implantation of slow release preparations on the conjuctive sac.

Because FIAC and FIAU are stable in an acid environment, such as is found in the human stomach, they can be formulated readily using pharmaceutically acceptable carriers well known in the art, with or without pH buffers, into dosages suitable for oral administration. Such carriers enable FIAU, its prodrug or metabolite to be formulated as tablets, pills, capsules, liquids, gels, syrups, suspensions and the like, for oral ingestion by a patient to be treated for infection or disease caused by HSV. With proper choice of carrier and suitable manufacturing practice, the compositions of the present invention, in particular, those formulated as solutions, may also be administered parenterally, such as by intravenous, subcutaneous or intramuscular injection.

Pharmaceutical compositions within the scope of the present invention include compositions wherein the active ingredient is contained in an effective amount to achieve its intended purpose. Determination of the effective amounts is well within the capability of those skilled in the art, especially in light of the detailed disclosure provided herein.

In addition to the pyrimidine nucleosides of the present invention, these pharmaceutical compositions may contain suitable pharmaceutically acceptable carriers comprising excipients and auxiliaries which facilitate processing of the active compounds into preparations which can be used pharmaceutically. Preferably, the preparations are formulated for oral administration, and are in the form of tablets, dragees, and capsules. Alternatively, the preparations may be administered rectally, such as in the form of suppositories. Alternatively, solutions may be prepared for oral or parenteral administration. Topical preparations such as solutions, creams, ointments, or gels may also be utilized. The compositions of the present invention contain from about 0.1 to about 50 mg of FIAU, its prodrug or metabolite, with the balance comprising the components of the pharmaceutical carrier. Preferably, the compositions of the present invention contain 0.5, 1, 2, 4, 8, 10, 15, 20, or 30 mg of FIAU, its prodrug or metabolite.

The pharmaceutical compositions of the present invention may be manufactured in a manner that is itself known, e.g., by means of conventional mixing, granulating, dragee-making, dissolving, levitating, emulsifying, encapsulating, entrapping or lyophilizing processes. Thus, pharmaceutical preparations for oral use can be obtained by combining the active compounds with solid excipients, optionally grinding a resulting mixture, and processing the mixture of granules, after adding suitable auxiliaries, if desired, to obtain tablets or dragee cores.

Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Additional auxiliaries that can be used include, but are not limited to, flow-regulating agents and lubricants, such as silica, talc, stearic acid or salts thereof such as magnesium or calcium stearate, and/or polyethylene glycol. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Possible pharmaceutical preparations which can be used rectally or vaginally include, for example, suppositories, which consist of a combination of the active compounds with a suppository base. Suitable suppository bases are, for example, natural or synthetic triglycerides, paraffin hydrocarbons, polyethylene glycols or higher alkanols. In addition, it is also possible to use gelatin rectal capsules that consist of a combination of the active compounds with a base. Possible base materials include, for example, liquid triglycerides, polyethylene glycols, or paraffin hydrocarbons.

For topical preparations, the active ingredient may be formulated in an ointment, emulsion, cream, gel, powder, spray, foam, or topical solution.

Water-soluble ointments, containing 0.1–10% active agent in a mixture of polyethylene glycols, and lipid-soluble ointments, containing a similar amount of active agent in petrolatum, may be prepared as preferred formulations for topical use. Creams containing 0.1–5% active agent and consisting of water (50%), emulsifying agents, such as glyceryl monostearate and polysorbate 80, cetyl alcohol, acting as a surface active agent stabilizing the emulsion, stiffening agents, such as wax microcrystalline, Softisan® 601 stiffening agent, paraffin and stearic acid, and suitable solvents, such as polyethylene glycol 300 and propylene glycol, may be especially useful. Other useful topical preparations are gels containing 0.1–5% of active agent in hydroxypropyl cellulose, serving as a gelling agent (4%), water (35%), alcohol (50%), and glycerin (10%). Topical solutions, containing 0.1–5% active agent in a mixture of alcohols (ethanol, 46%; polyethylene glycol-400, 44%; and propylene glycol, 5%), and suppositories, containing 0.1–5% active agent in polyethylene glycol 1000 (50–98%) and polyethylene glycol 3350 (2–30%), are also viewed as preferred topical formulations.

One of the preferred formulations of the compositions of the present invention are flavored syrups that contain about 1 to about 10 mg of active substance per ml of syrup. Thus, in a particular embodiment of the present invention, a flavored syrup comprises about 0.1 to about 1 percent by weight of the syrup (wt %) FIAU or FIAC, about 5–50 wt % purified water USP, about 5–50 wt % glycerin USP, about 5–50 wt % alcohol USP, about 5–50 wt % propylene glycol USP. In addition, the syrup also comprises about 0.0001–0.01 wt % of a coloring agent or combinations thereof, such as FD&C Red #40, FD&C Yellow #5 or FD&C Blue #1, about 0.01–0.1 wt % flavoring agents, such as artificial or natural Gran Marnier, orange, cherry, vanilla, strawberry, raspberry, lemon or chocolate flavor. Moreover, commercially available syrup additives, such as Syrup NF qs ad or Maltitol syrup, are preferably present at about 0.01 to about 0.1 wt %.

As mentioned, previously above, pharmaceutical preparations may also be prepared for parenteral administration. Suitable formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides. Aqueous injection suspensions may contain substances which increase the viscosity of the suspension, such as sodium carboxymethyl cellulose, sorbitol, or dextran. Optionally, the suspension may also contain suitable stabilizers.

Specific examples of the pharmaceutical compositions of the present invention are presented in further detail in the Examples Section of the present specification.

4.2. Dosage Regimens

A number of different herpes virus infections which are resistant to treatment with acyclovir may be treated in accordance with the invention, including but not limited to HSV-1, HSV-2, VZV and CMV. For example, HSV-1 or HSV-2 infections may be treated systemically, or topically. With respect to topical applications, ophthalmic preparations of FIAU or its prodrug may be utilized for HSV infection of the cornea. Alternatively, suppositories may be used to treat vaginal herpes infections. In another embodiment, HSV infections of oral mucosa may be treated using ointment preparations. In any of the foregoing infections, a systemic treatment such as intravenous preparations could be used.

The precise dosage amounts to be administered will be determined by routine experimentation. In particular, lower dosage regimens are preferred which range from about 0.05 to about 10 mg/kg-day. Most preferably, dosage levels of about 0.5 to about 5 mg/kg-day are to be administered continuously for about two weeks.

Alternatively, dosage levels of active ingredient are administered to HSV-infected patients to achieve a steady state antivirally effective peak plasma concentration of FIAU, its prodrug or metabolite in the range of about 0.1 to about 1 $\mu$g/ml. Indeed, it is anticipated that the active intracellular form of FIAU (or, possibly, also its metabolite, such as FAU) is the triphosphate. Hence, the present invention contemplates compositions that, when administered at certain dosage levels, provide or maintain intracellular amounts of the triphosphate form of the active ingredient which are effective to inhibit HSV.

4.3. Summary of Results of Studies on In Vitro Activities of FIAU and FIAC Against ACV-sensitive and -resistant Strains of HSV-1 and HSV-2

The antiviral activities of FIAU and FIAC against twenty four ACV-sensitive and -resistant strains of HSV-1 and HSV-2 were measured using a plaque reduction assay in human foreskin fibroblast (HFF) cells (Kern, E. R. et al, *J. Infect. Dis.* 1973, 128:290–229). This assay involved mixing serial two-fold dilutions of each of the three antiviral drugs in twice concentrated minimal essential media (MEM) with an equal volume of 1% agarose, applying the resulting mixture to monolayer cultures of HFF cells one hour after infection with 25–50 PFU of each of the virus strains, allowing the resulting cell culture to incubate for 72 hours, staining it with neutral red, counting plaques that formed as a result of infection, and calculating $EC_{50}$ levels, which were defined as the concentration of drug that resulted in 50% reduction of the number of plaques in the control plates. As shown in Table I, FIAU and FIAC were extremely active against ACV-sensitive strains of HSV-1, producing $EC_{50}$ values of 0.01–0.07 $\mu$g/ml; ACV gave $EC_{50}$ values of 0.2–2 $\mu$g/ml. Against ACV-resistant strains of HSV-1, FIAU and FIAC gave $EC_{50}$ values of 0.06–15.3 $\mu$g/m (for three viral strains, $EC_{50}$ values of 0.06–0.6 were observed); the ACV $EC_{50}$ values were greater than 40 $\mu$g/ml. FIAU and FIAC were extremely potent inhibitors of both ACV-sensitive and ACV-resistant strains of HSV-2. Against ACV-sensitive strains, FIAU and FIAC gave $EC_{50}$ values of 0.01–0.08 $\mu$g/ml; ACV showed $EC_{50}$ values of 0.3–0.7 $\mu$g/ml. Against ACV-resistant HSV-2 strains, ACV produced $EC_{50}$ values in excess of 13 $\mu$g/ml (primarily in excess of 100 $\mu$g/ml); FIAC and FIAU inhibited nine of these viral strains with $EC_{50}$. in the range of 0.04–1.3 $\mu$g/ml and four with $EC_{50}$ values between 3.6–24 $\mu$g/ml.

4.4. Summary of Results of Studies on Topical Treatment of Genital HSV-2 Infections in Guinea Pigs With FIAU or FIAC and Their Relevance in the Treatment of Genital HSV-2 Infections in Humans Intravaginal inoculation of guinea pigs with HSV-2 results in a primary genital infection involving viral replication in the vaginal tract followed by the development of lesions on the vaginal external genital skin surface. This infection is very similar in many respects to the primary HSV-2 infection of humans. Studies on the topical treatment of HSV-2 infections have shown a good correlation between the results of guinea pig animal studies and subsequent human trials (Kern, E. R. Herpesvirus, pages 617–636; ©1984 Alan R. Liss, Inc.). Guinea pigs were thus used as an animal model system for an investigation of the feasibility of treatment of HSV infections with FIAU or FIAC.

Groups of 10 weanling guinea pigs were infected intravaginally with each of an ACV-sensitive and an ACV-resistant HSV-2 virus preparation. Intravaginal inoculation with HSV-2, results in a primary genital infection followed by development of external vesicular lesions. The infected animals were treated with an ointment containing 10, 5, or 1% of either FIAU or FIAC, 24 hours after viral inoculation, both intravaginally and on the external genital skin. The response to this treatment was evaluated in two ways. One involved evaluation of HSV-2 replication in the vaginal tract by collection of vaginal secretions on days 1, 3, 5, 7, and 10 following inoculation and measuring their viral titer in a rabbit kidney cell microtiter CPE assay. A second technique, which was used to estimate efficacy, involved the visual examination of external genital lesions; lesions were graded on a 0–5+ score over a period of 21 days after viral inoculation. The results of these viral replication and lesion development studies were compared with the corresponding results for placebo-treated and control animals in order to determine the efficacy of treatment of HSV-2 infections with FIAU or FIAC.

Topical FIAU preparations containing 5% FIAU were as effective as a preparation containing 5% ACV in significantly reducing viral replication in the vaginal tract of animals infected with the ACV-sensitive strain of HSV-2 while 10% FIAU was more potent.

In animals infected with an ACV-resistant strain of HSV-2 (12247), treatment with 10% or 5% FIAU, but not 1% FIAU, significantly reduced vaginal viral production. The 5% ACV preparations had no effect on vaginal replication of HSV-2 (12247) with respect to area under virus-titer-day curve or mean peak virus titer.

Treatment of animals infected with the ACV-sensitive strain of HSV-2 with 5% FIAC was as effective as treatment with 5% ACV in significantly reducing viral replication in the vagina. No significant reduction in viral growth was observed upon treatment with 1% FIAC in comparison to placebo ointment.

In animals infected with the ACV-resistant 12247 strain of HSV-2, treatment with 5% FIAC significantly reduced both the area under the vaginal virus titer-curve and mean peak titer-curve. Treatment with 5% ACV had no effect on vaginal viral replication with respect to either measurement.

Figure 2:
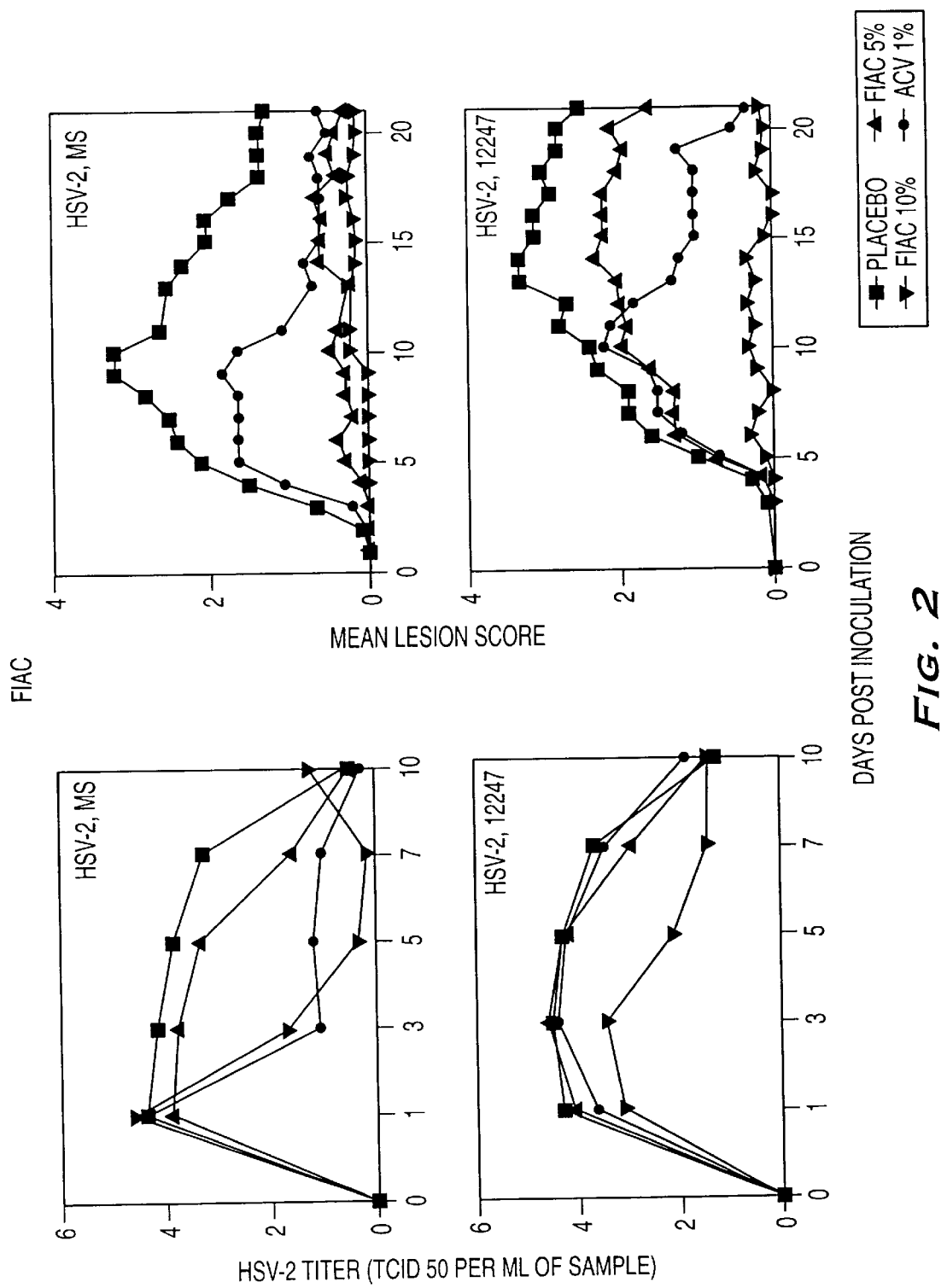
FIG. 2. The four panels of FIG. 2 show the inhibition of ACV-resistant and ACV-sensitive strains of HSV by FIAC.

The striking levels of inhibition of ACV-sensitive and -resistant strains of HSV by FIAU and FIAC are further demonstrated in FIGS. I and 2, which show the response of infection of guinea pigs by the HSV-2 strains MS (ACV-sensitive) and 12247 (ACV-resistant) to each of FIAU and FIAC, respectively, as a function of time. The four diagrams of FIG. I strikingly demonstrate the fact that ointments containing 5% and 10% FIAU are significantly more effective than ointments containing 5% ACV in reducing both virus titer and external lesions. The corresponding four diagrams of FIG. 2, with equal emphasis, demonstrate the superior effect of ointments containing 5% FIAC in reducing both virus titer and external lesions. FIG. 2 also shows that although 1% FIAC reduces the viral titer of HSV-2 MS less effeciently than 5% ACV, it is significantly more effective than ACV in reducing the severity of external lesions.

In addition, it was found that in animals infected with the ACV-sensitive strain of HSV-2, treatment with 10%, 5%, or 1% FIAU, or with 5% or 1% FIAC, was more effective than 5% ACV in controlling the extent of genital lesion development as measured by the area under the lesion score-day curve during infection. While ACV significantly reduced lesion development compared to placebo-treated animals (about 50%), the effect was considerably less than that observed for FIAU or FIAC treated animals.

In animals infected with the ACV-resistant 12247 strain, therapy with 1% FIAC, or with 5% ACV statistically reduced lesion development to a moderate degree. However treatment with 5% FIAC was much more effective than either treatment suppressing the lesion area by about 95%. Similarly, in animals inoculated with the ACV-resistant virus, therapy with 10%, 5%, or 1% of FIAU significantly reduced external lesions (by about 95% from control) and was considerably superior to treatment with 5% ACV, which suppressed the lesion score by about 50%.

In addition to the above investigations of FIAC and FIAU, the irritancy and toxicity of these drugs was evaluated by treating uninfected animals with each of the drugs on the same schedule as the infected animals. No signs of any irritation of the genital area or any other type of toxicity were observed.

5. EXAMPLES OF ANTIVIRAL COMPOSITIONS

5.1. Water-Soluble FIAU Ointment

1–100.0 mg/g

| Typical Component | FIAU Ointment, 5% | | |
|---|---|---|---|
| | mg/g | % | % Range |
| FIAU | 50.0 | 5.0 | 0.1–10.0 |
| Propylene Glycol | 50.0 | 5.0 | 1.0–10.0 |
| Polyethylene Glycol-3350, USP | 240.0 | 24.0 | 10.0–40.0 |
| Polyethylene Glycol-400, USP qs ad | 660.0 | 66.0 | 40.0–80.0 |

Excipient Rationale

Propylene Glycol, USP—Co-solvent/Preservative;
Possible substitutions: Glycerin, ethanol, isopropyl alcohol or other alcohols, polysorbates.
Polyethylene Glycol-3350, USP—Viscosity increasing agent; Possible substitutions:
Polyethylene glycol—900, 1000, 1450, 4500, 8000 or other high molecular weight glycols, stearyl alcohol, polyoxyl 40 stearate.
Polyethylene Glycol—400, USP—Solvent; Possible substitutions: Polyethylene glycol 200, 300, 600, or other low molecular weight glycols.

Method of Manufacture

1. Add a portion (~50%) of the polyethylene glycol—400 to a suitable tared stainless steel mixing bowl fitted with a variable speed agitator and a source of heat.
2. Add the polyethylene glycol-3350 to the bowl and warm gently to ~50° C. with gentle agitation. Continue stirring until the mixture has melted and a complete solution is obtained.
3. Add the propylene glycol, USP and FIAU to the solution in Step 2 and stir to mix well.
4. Q.S. to the final weight with polyethylene glycol-400 and blend to achieve a uniform, clear solution.
5. Remove the heat and permit the solution to cool slowly, continuing gentle agitation until the solution has congealed to a smooth homogeneous ointment and the temperature is below 35° C.

5.2. FIAU Petrolatum Ointment

1–50.0 mg/g

| Typical Component | FIAU Petrolatum Ointment, 1.0% | | |
|---|---|---|---|
| | mg/g | % | % Range |
| FIAU | 10.0 | 1.0 | 0.1–5.0 |
| White Wax | 50.0 | 5.0 | 1.0–10.0 |
| White Petrolatum | 940.0 | 94.0 | 85.0–98.9 |

Excipient Rationale

White wax—Stiffening agent; Possible substitutions: Yellow wax or beeswax, paraffin wax or other commercial substitutions.
White Petrolatum—Ointment Base; Possible substitutions: Yellow Petrolatum or other commercial substitutes.

Method of Manufacture

1. Combine white wax and white petrolatum into a suitable container and heat gently to obtain a clear uniform mixture.
2. Add FIAU to the mixture obtained in Step 1 and mix until thoroughly dispersed (~15 min @80° C.).
3. Remove the heat and permit the solution to cool slowly while mixing until the solution has congealed to a smooth homogeneous ointment and the temperature is below 35° C.

5.3. FIAU Cream 1.0–50.0 mg/g

| Typical Components | FIAU Cream, 1.0% | | |
|---|---|---|---|
| | mg/g | % | % Range |
| FIAU | 10.0 | 1.0 | 0.1–5.0 |
| Purified Water, USP | 500.0 | 50.0 | 20.0–80.0 |
| Cetyl Alcohol, USP | 80.0 | 8.0 | 2.0–16.0 |
| Wax, Microcrystalline, USP | 80.0 | 8.0 | 2.0–16.0 |
| Polysorbate 80, USP | 50.0 | 5.0 | 1.0–10.0 |
| Polyethylene Glycol-300, USP | 50.0 | 5.0 | 1.0–10:0 |
| Propylene Glycol, USP | 50.0 | 5.0 | 1.0–10.0 |
| Softisan-601 ® stiffening agent | 60.0 | 6.0 | 1.0–12.0 |
| Stearic Acid, USP | 40.0 | 4.0 | 1.0–10.0 |
| Paraffin, USP | 30.0 | 3.0 | 1.0–6.0 |
| Glyceryl Monostearate, USP | 30.0 | 3.0 | 1.0–6.0 |
| Octoxynol | 20.0 | 2.0 | 0.5–5.0 |

Excipient Rationale

Purified Water—To aid solubility of the active ingredient and in the formation of the oil in water cream.

Cetyl Alcohol—Surface active agent used to stabilize the emulsions and imparts a smooth texture to the skin. Possible substitutions: Stearyl alcohol, octadecanol.

Wax Microcrystalline, Softisan® 601, paraffin and stearic acid—Stiffening agents. Possible substitutions: Yellow wax, beeswax or other commercial substitutions.

Polysorbate 80—Because of its hydrophilic and lyophilic characteristics it helps as an emulsifying agent. Possible substitutions: fatty acid esters of sorbitol and its anhydrides copolymerized with varying numbers of moles of ethylene oxide.

Polyethylene Glycol 300—to aid solubility of the active ingredient. Possible substitutions: other low molecular weight glycols.

Propylene Glycol—Solvent/Preservative. Possible substitutions: Glycerin, other alcohols.

Glyceryl Monostearate—Emulsifying agent; Possible substitutions: polyol fatty acid esters.

Octoxynol—Surfactant and emulsifying agent; Possible substitutions: Nonionic surfactants.

Method of Manufacture

1. Clean area and weigh out each component.
2. Add the polysorbate 80, Octoxynol, PEG 300 and propylene glycol together. Add approximately 70% of the FIAU and mix.
3. Melt the paraffin glyceryl monostearate, cetyl alcohol, stearic acid, wax and Softisan® 601 stiffening agent together.
4. Heat the water (50° C.) and add the remainder of the FIAU and stir to dissolve.
5. Heat the old phase (3) to approximately 80° C.
6. Heat water to 70° C.
7. Place water under Ross Misier, add the oil phase and mix. As the cream cools, transfer to the kitchen and allow to cool to room temperature with gentle mixing.

5.4. FIAU Gel 1.0–50.0 mg/g

| Typical Components | FIAU Gel, 1.0% | | |
|---|---|---|---|
| | mg/g | % | % Range |
| FIAU | 10.0 | 1.0 | 0.1–5.0 |
| Glycerin, USP | 100.0 | 10.0 | 1.0–25.0 |
| Hydroxypropyl Cellulose, NF | 40.0 | 4.0 | 0.5–8.0 |
| Purified Water, USP | 350.0 | 35.0 | 10.0–70.0 |
| Alcohol, SD40-2 qs ad | 500.0 | 50.0 | 20.0–75.0 |

Excipient Rationale

Glycerin—Co-solvent/Preservative; Possible substitutions: Propylene glycol, isopropyl alcohol, ethanol, methanol or other alcohols.

Hydroxypropyl Cellulose—Gelling Agent; Possible substitutions: Hydroxyethyl cellulose, hydroxypropyl methycellulose, methycellulose or other cellulosic agents, carbomer, polyvinyl alcohol, povidone, gelatin or other commercial substitutions.

Purified Water—Co-solvent.

Alcohol, SD40-2—Co-solvent; Possible substitutions: Alcohol USP, Isopropyl alcohol, methanol or other alcohols.

Method of Manufacture

1. Combine a portion of the water and alcohol (~75% of each) into a suitable container and mix well.
2. Add FIAU to the mixture obtained in Step 1 and mix until dissolved.
3. Combine the remaining water and glycerin into a suitable container and heat to approximately 50° C.
4. Add the hydroxypropyl cellulose, slowly, to the water/glycerin mixture (Step 3) to obtain a smooth slurry.
5. Add the hydroxpropyl cellulose slurry to the FIAU solution from Step 2.
6. Q.S. to the final weight with the alcohol and continue mixing for approx. 30 minutes, keeping the container covered to avoid evaporation.

5.5. FIAU Solution 1.0–50.0 mg/ml

| Typical Components | FIAU Solution, 5% | | |
|---|---|---|---|
| | mg/ml | % | % Range |
| FIAU | 50.0 | 5.0 | 0.1–5.0 |
| Propylene Glycol, USP | 50.0 | 5.0 | 1.0–10.0 |
| Polyethylene Glycol-400, USP | 440.0 | 44.0 | 10.0–80.0 |
| Alcohol, USP qs ad | 460.0 | 46.0 | 10.0–80.0 |

Excipient Rationale

Propylene Glycol, USP—Co-solvent/Preservative; Possible substitutions: Glycerin, isopropyl alcohol, methanol or other alcohols, polysorbates.

Polyethylene Glycol-400—Co-solvent; Possible substitutions: Polyethylene glycol 200, 300, 600, or other low molecular weight glycols.

Alcohol, USP—Solvent; Possible substitutions: Alcohol S40-2, isopropyl alcohol or other alcohols.

Method of Manufacture

1. Combine propylene glycol with polyethylene glycol in a suitable container and stir to obtain a uniform solution.
2. Add a portion (~⅔) of the alcohol to Step 1 and mix well.
3. Add FIAU to Step 2, rinsing the container well with a portion of the remaining alcohol.
4. Q.S. to the final volume with the alcohol and mix well to obtain a clear solution.

5.6. FIAU Suppositories

Suppository dosage forms containing FIAU or FIAC suitable for vaginal or rectal administration as an anti-viral treatment are described.

A typical preparation in a water soluble base is as follows:

| | % | Wt. gm |
|---|---|---|
| Polyethylene Glycol 1000 | 95 | 47.5 |
| Polyethylene Glycol 3350 | 4 | 2.0 |
| FIAU | 1 | 0.5 |

Weigh the components and place the PEG-1000 in a suitable vessel equipped with a heat source and agitation.

Heat the PEG-1000 with slow stirring to ~50° C. until the material has melted to a clear liquid. Maintaining the temperature at 40° C., add the PEG-3350 and continue stirring until the mixture melts to a clear liquid. Add the FIAU and mix until dissolved. Remove the heat and allow the mixture to cool with slow agitation until the mixture begins to congeal.

Mold the mass into suppositories using suitable mold. Package and maintain the finished suppositories in a cool place until use.

Excipient Rationale

BASE: Various ratios or mixtures of high and low molecular weight polyethylene glycols or other water miscible glycol polymers serve to dissolve the active anti-viral drug. The selection of the molecular weight of the polymer and ratios of these polymers permits the control and selection of the melting point and firmness of the resultant suppository. Various pharmaceutical additions, such as glycols and alcohols, water and gelling agents may be employed or substituted to modify the physical pharmaceutic characteristics of the suppository.

Alternatives, and using the same procedure, various pharmaceutically acceptable oils and waves may be employed to produce lipid based suppositories, such as cocoa better, other natural fat material or synthetic high melting petrolatum bases typically employed in the preparation of pharmaceutic rectal suppositories.

5.7. FIAC (Water-miscible suppository)

| Typical Component | mg/g | % Range |
|---|---|---|
| FIAC | 10.0 | 0.1 to 5.0 |
| Polyethylene Glycol 1000 | 960.0 | 50 to 98 |
| Polyethylene Glycol 3350 | 40.0 | 2 to 30.0 |

Excipient Rationale Polyethylene Glycol 1000: Solvent. Possible substitutions polyethylene glycol 900, 1000, 1450 or other high molecular weight glycols, stearyl alcohol. Polyethylene Glycol 3350: viscosity increasing agent. Possible substitutions polyethylene glycol 4000, 4500, 8000 or other high molecular weight glycols, polyoxyl 40 stearate.

Polyoxyethylene sorbiton fatty acid esters can also be included alone or in combination with other wax or fatty materials.

Method of Manufacture

The method used to prepare the FIAU suppositories (Section 5.6) was used.

5.8. FIAU (Water-miscible Suppository)

| Typical Component | mg/g | % Range |
|---|---|---|
| FIAU | 10.0 | 0.1 to 5.0 |
| Polyethylene Glycol 1000 | 960.0 | 50 to 98 |
| Polyethylene Glycol 3350 | 40.0 | 2 to 30.0 |

Excipient Rationale

Polyethylene Glycol 1000: Solvent. Possible substitutions polyethylene glycol 900, 1000, 1450 or other high molecular weight glycols, stearyl alcohol.

Polyethylene Glycol 3350: Viscosity increasing agent. Possible substitutions polyethylene glycol 4000, 4500, 8000 or other high molecular weight glycols, polyoxyl 40 stearate.

Polyoxyethylene sorbiton fatty acid esters can also be included alone or in combination with other wax or fatty materials.

Method of Manufacture

The method used to prepare the FIAU suppositories (Section 5.6) was used.

5.9. FIAU Syrup

An FIAU syrup formulation suitable for use as a pharmaceutical antiviral composition is described below. In particular, the syrup formulation is prepared by combining the components listed, with the amounts representative of the content of the listed component, respectively, in 1 ml of syrup.

| FIAU | 10 | mg |
|---|---|---|
| Glycerin, USP | 0.10 | ml |
| Alcohol, USP | 0.10 | ml |
| Propylene Glycol, USP | 0.10 | ml |
| Purified Water, USP | 0.10 | ml |
| FD&C Red #40 | 0.025 | mg |
| FD&C Yellow #5 | 0.010 | mg |
| FD&C Blue #1 | 0.001 | mg |
| Artificial Flavors | 0.001 | ml |
| Maltitol syrup qs ad | 1.0 | ml |

To a suitable vessel equipped with agitation and a heat source, add the glycerin, alcohol and propylene glycol. Mix for approximately five minutes to obtain a clear, homogeneous solution, while heating to approximately 40° C. Next add the FIAU (or FIAC, as the case might be), maintaining agitation and rinsing well with the purified water. Mixing is continued for at least twenty minutes or until a clear, complete solution is obtained. Next, add the coloring and flavoring agents, while maintaining agitation for five minutes. Let the mixture cool to room temperature, if necessary, and bring the mixture to the final volume with the maltitol syrup. Mix gently to avoid incorporation of air bubbles for an additional 30 minutes. The batch may be tightly covered and held for final filtration and packaging. Filter the syrup through a 1.0 micron membrane filter or equivalent and package in final containers.

The amount of the active ingredient can be adjusted so that variable amounts of antiviral agent can be administered per ml of syrup (e.g., 0.25, 0.5, 1 or 5 mg of FIAU).

Other examples of syrups, particularly flavored ones, are presented below.

| FIAU 10 mg/ml - Orange/Chocolate Flavor | | |
|---|---|---|
| FIAU | 10 | mg |
| Purified Water, USP | 0.10 | ml |
| Glycerin, USP | 0.10 | ml |
| Alcohol, USP | 0.10 | ml |
| Propylene Glycol, USP | 0.10 | ml |
| FD&C Red #40 | 0.025 | mg |
| FD&C Yellow #5 | 0.010 | mg |
| FD&C Blue #1 | 0.001 | mg |
| Artificial Gran Manier | 0.0005 | ml |
| Artificial Chocolate | 0.0005 | ml |
| Syrup NF qs ad | 1.0 | ml |

Excipient Rationale

Vehicle: Maltitol syrup, water, glycerin, alcohol and propylene glycol; possible substitutions include glucose, dextrose, mannitol, saccharin, sucrose, sorbitol, honey, mucilages, and other flavored syrups.

Flavors: Orange/vanilla, chocolate/grand marnier, and cherry; possible substitutions include raspberry, lemon, spearmint, or citric. This product can also contain no flavor.

Colors: FD & C Red #40, FD & C Blue #1 and FD & C Yellow #5. Other colors can be substituted or the product can be without colors.

Note: This product can contain preservatives or suitable buffering system.

| FIAC 10 mg/ml - Cherry/Orange Flavor | | |
|---|---|---|
| FIAU | 10 | mg |
| Purified Water, USP | 0.10 | ml |
| Glycerin, USP | 0.10 | ml |
| Alcohol, USP | 0.10 | ml |
| Propylene Glycol, USP | 0.10 | ml |
| FD&C Red #40 | 0.05 | mg |
| FD&C Yellow #5 | 0.10 | mg |
| Natural Orange Flavor | 0.0075 | ml |
| Artificial Vanilla | 0.0035 | ml |
| Maltitol syrup qs ad | 1.0 | ml |

Excipient Rationale

Vehicle: Maltitol syrup, water, glycerin, alcohol and propylene glycol; possible substitutions include glucose, dextrose, mannitol, saccharin, sucrose, sorbitol, honey, mucilages, and other flavored syrups.

Flavors: Orange/vanilla, chocolate/gran marnier, and cherry; possible substitutions include raspberry, lemon, spearmint, or citric. This product can also contain no flavor.

Colors: FD & C Red #40, FD & C Yellow #5. Other colors can be substituted or the product can be without colors.

Note: This product can contain preservatives or suitable buffering system.

5.10. Oral Solution

For initial investigation, FIAC will be administered as an oral solution, prepared prior to use. Solutions will be prepared by dissolving the FIAC Powder for Oral Solution (containing neat FIAC active ingredient) with purified water prior to administration.

Component: FIAC, 1-(2'-deoxy-2'-fluoro-β-D-arabinofuranosyl)-5-iodocytosine (neat)

Composition: FIAC will be provided in specified preweighed amounts (e.g., from about 0.05 to about 500 mg).

Packaging: Individually weighed doses of FIAC will be packaged in 4 oz. amber glass ovals (i.e., Owens-Illinois P-804)

Closure: Owens-Illinois Clic Lock® closure

5.10.1. Method of Preparation

The FIAC oral solution is prepared by the following procedure:

To each dosage unit of FIAC powder for solution:
a. Add 100 ml of purified water USP
b. Disperse with the aid of an ultrasonic bath (10 minutes) or by intermittent shaking (~30 minutes)
c. Observe individual bottles visually to assure complete solution prior to use
d. Maintain unused portion of prepared solution under refrigeration
e. Note: If refrigerated—carefully observe for complete solution and gently warm to room temperature with agitation (ultrasonic bath may be used if available) to redissolve if crystals are present
f. Discard any unused solution after one week from preparation

5.10.2. FIAC Powder for Oral Solution

General Methods of Manufacture and Distribution

Clean bottle by blowing with filtered compressed air (filter 0.45 u). Individually weigh and record FIAC for each dose on an analytical balance (i.e. Sartorius or equivalent). Afterward, transfer weighed dose of FIAC to clean bottle and check weight for complete transfer using individual bottle tare on a suitable balance (i.e. Mettler top load model) or equivalent. Finally, cap individual bottles after checking weight and hold for release and labeling.

The specifications for FIAC Powder for Oral Solution are treated as a unit dose due to the nature of the product. It is recognized that the resulting solution product is a multiple dose experimental dosage form.

The methods of testing are drawn directly from the assay procedure for active substance since the experimental unit contains only neat active substance.

| Specifications | Limits |
|---|---|
| Appearance | Crystalline powder, white to off-white |
| Identification, HPLC | Conforms with standard |
| Solution Description | Clear, colorless solution |
| Assay for FIAC and Related Substances | |
| FIAC | 95.0–105.0% of label claim |
| FIAU | 2.0% maximum |
| Other Related Substances | 2.0% maximum |

5.11. One, Five and Ten Milligram Capsules

Lower dosage range capsules were prepared as follows. Due to content uniformity considerations, a new technique referred to as Moisture Activated Dry Granulation, MADG, was used to prepare the capsule blends. This technique is briefly described below:

MADG combines the ease of manufacture of a direct blend formulation with the advantages of a wet granulation. A modified version of the agglomeration step in wet granulation is utilized, however, no drying step is required. Briefly, this granulation technique involves blending the drug with an excipient ("carrier"—e.g. lactose) and a dry binder (e.g., PVP). This blend is then moistened using a small amount of water (1–3% of the formula weight). This moisture activates the dry binder and makes the drug adhere to the carrier particles. Moisture distributing agents (e.g. microcrystalline cellulose) and additional excipients are then added and the granulation process is complete. The resultant granulation provides good content uniformity as well as a free flowing blend for encapsulation or tabletting.

The choice and levels of excipients for the low dosage capsules can be determined as needed by one skilled in the art. Also, the FIAU bulk can be passed through a 200 mesh screen rather than a 100 mesh screen for content uniformity considerations.

5.12. FIAU Sodium Salt

FIAU sodium salt for injection is a lyophilized sodium salt of FIAU. The sodium salt is prepared by allowing FIAU to react with sodium hydroxide in situ during preparation of the solution for lyophilization. The lyophilized cake is white in color.

A clinical lot of FIAU sodium salt for injection was reconstituted for stability studies with Sterile Water for Injection, USP, 0.9% Sodium Chloride Injection, USP, and 5% Dextrose Injection, USP. The solutions were stored at room temperature (25° C.). Chemical potency, impurities and degradation products were monitored by HPLC. The solution pH and physical appearance were also monitored. The chemical potency data were statistically analyzed.

These studies support a utility time of 48 hours storage at room temperature (25° C.) for the following diluents and concentrations, provided that the preconstituted vials have been stored at room temperature (25° C.) and have not aged beyond their expiration date.

Each vial was reconstituted with 2.2 ml of Sterile Water for Injection, USP, yielding a solution concentration of 50 mg/ml. Lower concentrations can be prepared with the appropriate adjustments of the respective components.

Alternatively, the above solution when further diluted with Sterile Water for Injection, USP, 0.9% Sodium Chloride Injection, USP or 5% Dextrose Injection, USP, yielded a solution concentration of 0.2–5 mg/ml.

5.13. FIAU Capsule (1–10 MG)

| Typical Components | | | |
|---|---|---|---|
| FIAU | 3.03% | 10.00 | 1–10 |
| Microcrystalline Cellulose (Avicel ®) | 20.0% | 66.00 | 59–73 |
| Magnesium Sterate, USP | 0.5% | 1.65 | 1.5–1.8 |
| Explotab ® disintegrant | 2.0% | 6.60 | 5.9–7.3 |
| Lactose, Hydrous USP qs ad | 76.0% | 250.80 | 225–275 |
| Fill Weight | | 330 mg | |
| Capsule Size | | #1 | |

Excipient Rationale
 a. Diluent—microcrystalline cellulose (Avicel®), lactose, hydrous. Possible substitutions: Lactose, anhydrous.
 b. Lubricant—magnesium sterate. Possible substitutions: Talc, calcium sterate, stearic acid, magnesium salts.
 c. Disintegrant—Explotab® disintegrant. Possible substitutions: Starch, providone XL, sodium starch glycolate, croscarmelose, methylcellulose, carboxymethyl cellulose.

Method of Manufacture
 a. Mix FIAU with an equal portion of lactose.
 b. Gradually add remainder of lactose and mix well.
 c. Combine Avicel® microcrystalline cellulose, Explotab® disintegrant and magnesium sterate and mix well.
 d. Combine the FIAU/lactose mixture (Step 2) with the Avicel® mixture (Step 3) and mix until sufficiently blended (~10 min. minimum).

5.14. FIAU Tablets (1–10 mg)

Wet Granulation/Direct Compression Method

| Typical Components | % | % Range | FIAU Tablet, 5 mg. mg/cap | FIAU Tablet, 10 mg. mg/cap |
|---|---|---|---|---|
| FIAU (5%) | a | 0.25–5 | 5 | 10 |
| Lactose (55%) | a | 40–70 | — | — |
| PVP (15% in water) | a | 10–20 | 60.5 | 60.5 |
| Avicel PH101 microcrystalline cellulose | 56.5% | 40–75 | 565 | 565 |
| Lactose | 31.0% | 20–50 | 310 | 310 |
| Explotab ® disintegrant | 5.0% | 2–10 | 50 | 50 |
| Sterotex K | 1.0% | 0.5–5 | 10 | 10 |
| Magnesium Stearate, USP | 0.5% | 0.2–2 | 5 | 5 |
| Net Tablet Weight | | | 200 mg | 400 mg | a = The combined percentage of the first three items is 6%.

Excipient Rationale
 a. Diluent—lactose, hydrous. Possible substitutions: Lactose, anhydrous, microcrystalline cellulose (Avicel®).
 b. Lubricant—magnesium stearate; possible substitutions: Talc, calcium stearate, stearic acid, magnesium salts.
 c. Disintegrant—possible substitutions. Starch, providone XL, sodium starch glycolate, methylcellulose, carboxymethyl cellulose.
 d. Binder—Sterotex K. Possible substitutions: Starch, gelatin, sugars (sucrose, glucose, etc.), carboxymethylcellulose, methylcellulose, polyvinyl pyrrolidone.

Method of Manufacture
 a. Mix the FIAU and lactose together, wet the mixture with the 15% Solution of PVP in water.
 b. Dry the granulation overnight at 40° C.
 c. Pass the dried granulation through a 10 mesh screen and then through a 20 mesh screen.
 d. Mix the magnesium stearate and sterotex K together and then add the explotab.
 e. Combine the two mixtures obtained in Step c and d above.
 f. Add the Avicel microcrystalline cellulose, lactose and mixture obtained in Step e to dry blender.
 g. Allow the mixture to blend for 15 minutes.
 h. Compress the tablet to the specified weight.

| Description | 1 mg Tablet | 2 mg Tablet |
|---|---|---|
| Diameter | 9 mm | 9 mm |
| Thickness | 4.0 ± 0.5 mm | 6.0 ± 0.5 mm |
| Hardness | 3–10 kg | 3–10 kg |

5.15. FIAU Tablets (1–10 mg)

Direct Compression Method

| Typical Components | % | % Range | FIAU Tablet, 5 mg. mg/cap | FIAU Tablet, 10 mg. mg/cap |
|---|---|---|---|---|
| FIAU (100 mesh) | 2.5% | 0.5–2.5 | 5 | 10 |
| Avicel PH101 | 55.0% | 40–75 | 110 | 220 |

-continued

| Typical Components | % | % Range | FIAU Tablet, 5 mg. mg/cap | FIAU Tablet, 10 mg. mg/cap |
|---|---|---|---|---|
| microcrystalline cellulose Lactose, Hydrous USP | 36.0% | 25–55 | 72 | 144 |
| Explotab ® disintegrant | 5.0% | 2–10 | 10 | 20 |
| Sterotex K | 1.0% | 0.5–5 | 2 | 4 |
| Magnesium Stearate, USP | 0.5% | 0.2–2 | 1 | 2 |
| Net Tablet Weight | | | 200 mg | 400 mg |

Excipient Rationale a. Diluent—microcrystalline cellulose (Avicel®), lactose, hydrous. Possible substitutions: Lactose, anhydrous.

b. Lubricant—magnesium stearate; possible substitutions: Talc, calcium stearate, stearic acid, magnesium salts.

c. Disintegrant—Explotab®; possible substitutions: Starch, providone XL, sodium starch glycolate, croscarmelose, methylcellulose, carboxymethyl cellulose.

d. Binder—Sterotex K, possible substitutions: starch, gelatin, sugars (sucrose, glucose, etc.), carboxymethylcellulose, methylcellulose, polyvinyl pyrrolidone.

Method of Manufacture a. Mix the magnesium stearate and Sterotex K in a plastic bag.

b. Add the Explotab® disintegrant to the mixture obtained in Step b.

c. Add the FIAU to the mixture obtained in Step b.

d. Add the Avicel PH101 microcrystalline cellulose, lactose and the mixture obtained in Step c in layers in the twin shell dry blender.

e. Mix for 15 minutes.

f. compress the tablet at the specified weight.

| Description | 1 mg Tablet | 2 mg Tablet |
|---|---|---|
| Diameter | 9 mm | 9 mm |
| Thickness | 3.5 ± 0.5 mm | 7.0 ± 0.5 mm |
| Hardness | 3–10 kg | 3–10 kg |

6. In Vitro Activity of FIAU Against and FIAC Against ACV-Sensitive and ACV-Resistant HSV Strains The in vitro experiments and results outlined below demonstrate that FIAU and FIAC are effective against both ACV-sensitive and -resistant strains of HSV-1 and HSV-2.

The following assay was used to evaluate the anti-HSV properties of FIAU, FIAC and ACV.

6.1. Plaque Reduction Assay for HSV-1 and HSV-2 using Semi-Solid overlay

Two days prior to use, HFF cells are plated into six well plates and incubated at 37° C. with 5% $CO_2$ and 90% humidity. One the date of assay, the drug is made up at twice the desired concentration in 2× MEM and then serially diluted 1:5 in 2X MEM using six concentrations of drug. The initial starting concentration is usually 200 μg/ml down to 0.06 μg/ml. The virus to be used is diluted in MEM containing 10% FBS to a desired concentration which will give 20–30 plaques per well. The media is then aspirated from the wells and 0.2 ml of media being added to drug toxicity wells. The plates are then incubated for one hour with shaking every fifteen minutes. After the incubation period, an equal amount of 1% agarose was added to an equal volume of each drug dilution. This will give final drug concentrations beginning with 100 μg/ml and ending with 0.03 μg/ml and a final agarose overlay concentration of 0.5%. The drug agarose mixture is applied to each well in 2 ml volume and the plates then incubated for three days, after which the cells were stained with a 1.5% solution of neutral red. At the end of 4–6 hr incubation period, the stain is aspirated, and plaques counted using a stereomicroscope at 10× magnification.

6.2. Assay Results

The results of the plaque reduction assay described above for ACV, FIAU, and FIAC, expressed as $EC_{50}$ values, are summarized in Table I.

TABLE I

SUSCEPTIBILITY OF HSV ISOLATES TO ACV, FIAU, AND FIAC

| | | $EC_{50}$ (μg/ml)[a] | | |
|---|---|---|---|---|
| Virus strain | TK Phenotype | ACV | FIAU | FIAC |
| HSV-1 | | | | |
| E-377 | positive | 0.20 | 0.02 | 0.06 |
| SC 16 | positive | 0.20 | 0.04 | 0.05 |
| SC 16-S1 | altered | 91.0 | 0.14 | 0.06 |
| PAAr[5] | positive[b] | 2.0 | 0.02 | 0.07 |
| DM 2.1 | deficient | >100 | 8.9 | 9.3 |
| 11893 | altered | 40. | 0.08 | 0.6 |
| 13231 | positive | 0.30 | 0.01 | 0.04 |
| 11359 | deficient | >100 | 2.1 | 15.3 |
| 13545 | positive | 0.78 | 0.01 | 0.04 |
| 11360 | deficient | 85.0 | 0.03 | 0.50 |
| B-2006 | deficient | >100 | 2.50 | 10.50 |
| HSV-2 | | | | |
| MS | positive | 0.70 | 0.01 | 0.07 |
| 8705 | positive | 0.34 | 0.03 | 0.05 |
| 8707 | altered | 34.0 | 0.04 | 0.5 |
| 8711 | deficient | >100 | 3.7 | 4.3 |
| 12247 | altered | >100 | 0.19 | 1.3 |
| 11680 | altered | 13 | 0.03 | NT[c] |
| 13386 | positive | 0.30 | 0.01 | 0.08 |
| 13546 | positive | 0.30 | 0.02 | 0.05 |
| 11575 | partial | >100 | 3.6 | 24. |
| 11572 | partial | >100 | 0.80 | 5.9 |
| 11361 | deficient | >100 | 0.80 | 22. |
| AG-3 | deficient | >100 | 0.09 | 0.30 |
| 11785 | partial | 24. | 0.02 | NT[c] |

[a] Plaque reduction assay in HFF cells, mean of 2 assays.
[b] Polymerase mutant.
[c] Not tested.

7. Studies on Topical Treatment of Genital HSV-2 Infections in Guinea Pigs With FIAU or FIAC

7.1. Materials and Methods

7.1.1. Antiviral Preparations

Ointments, such as those described in Section 5, containing 1%, 5%, or 10% FIAU or FIAC, and a similar preparation containing 5% ACV in polyethylene glycol, obtained from the Hospital Pharmacy of The University of Alabama at Birmingham, were used.

7.2. Genital HSV-2 Infection of Guinea Pigs

7.2.1. Description of the Model

Intravaginal inoculation of weanling guinea pigs with HSV-2 results in a primary genital infection characterized by initial replication of virus in the vaginal tract followed by the development of external vesicular lesions. Virus titers peak on days one to three in the vaginal tract and gradually clear by days 7–10. The external genital lesions first appear on day four, peak lesion severity occurs on days 6–8, and the lesions generally heal by days 15–18. In this model infection using HSV-2 that is sensitive to ACV, treatment with topical or oral ACV against primary disease was completely predictive of the efficacy in subsequent human trials.

7.2.2. Virus and Viral Inoculation

In addition to wild type MS strain, a strain of HSV-2 (12247) that has an altered thymidine kinase and is resistant to ACV in cell culture was utilized for animal inoculation. Female Hartley guinea pigs (Charles River, Kingston, N.Y.) weighing 250–300 g were inoculated intravaginally (i.vag.) one hour after being swabbed for removal of vaginal secretions. Viral inoculation was accomplished by inserting a swab soaked with virus into the vaginal tract and rotating approximately six times. Animals were inoculated with virus preparations that titered $6.2 \times 10^5$ plaque forming units (pfu) per/ml for the MS strain of HSV-2 or $1.2 \times 10^5$ pfu/ml for the 12247 strain of HSV-2.

7.2.3. Treatment of Guinea Pigs

Groups of 10 guinea pigs were treated both i.vag. and on the external genital skin with 0.1 ml (total of 0.2 ml per animal per treatment) of each preparation. Animals were treated three times daily for six days (FIAU) or for seven days (FIAC) beginning 24h post-viral inoculation. Three uninfected animals were treated with each preparation on the same schedule to assess local toxicity.

7.2.4. Sample Collection, Virus Assays, and Development of Genital Lesions

To determine the effect of treatment on HSV-2 replication in the vaginal tract, swabs of vaginal secretions were obtained during the primary infection on days 1, 3, 5, 7, and 10 after HSV-2 inoculation. The swabs were placed in tubes containing 2.0 ml of media, and frozen at $-70°$ C. until titrated for HSV. When all samples were collected, they were thawed, vortexed, diluted serially, and HSV-2 titers determined in rabbit kidney cells using a microtiter CPE assay. Another measure for determining efficacy of treatment is the development and severity of external genital lesions. Severity of lesions was graded on a 0–5+ score. The presence or absence and severity of lesions was recorded for 21 days after viral inoculation.

7.2.5. Evaluation of Efficacy

Infection rates, peak lesion scores, peak virus titers, areas under virus titer-day and lesion score-day curves between placebo-treated and drug-treated animals were compared using the Mann-Whitney U rank sum test. A p-value of 0.05 or less was considered significant.

7.3. RESULTS

7.3.1. Genital Irritation of FIAU or FIAC Preparations in the Guinea Pig

There were no signs of any irritation of the genital area or any other toxicity in uninfected placebo-ointment, FIAU or FIAC treated animals. The animals remained healthy and normal in appearance throughout the observation period.

7.3.2. Effect of Topical Treatment with FIAU or FIAC Preparations on Vaginal Viral Replication in the Guinea Pig The effect of topical treatment with FIAU preparations on vaginal viral replication is shown in TABLE III. In animals infected with the ACV-sensitive strain of HSV-2 (MS), therapy with 10% or 5% FIAU was as effective as 5% ACV in significantly reducing viral replication in the vaginal tract. A marginal effect was observed with 1% FIAU.

In animals inoculated with the ACV-resistant strain of HSV-2 (12247), again, treatment with 10% or 5% FIAU, but not 1% FIAU, significantly altered vaginal virus replication. In contrast, 5% ACV had virtually no effect on vaginal virus titers.

The effect of topical treatment with FIAC preparations on vaginal viral replication is shown in TABLE IV. In animals infected with the ACV-sensitive MS strain of HSV-2, therapy with 5% FIAC was as effective as 5% ACV in significantly altering vaginal viral replication. No effect was observed with 1% FIAC.

In animals infected with the ACV-resistant 12247 strain of HSV-2, only treatment with 5% FIAC significantly reduced vaginal virus titers. In this model, treatment with 1% FIAC or 5% ACV had no effect on vaginal viral replication.

7.3.3. Effect of Topical Treatment with FIAU or PIAC Preparations on Lesion Development in the Guinea Pig The effect of topical treatment with the FIAU preparations on lesion development is summarized in TABLE V. In animals infected with the ACV-sensitive strain of HSV-2 (MS), therapy with 10%, 5% or 1% FIAU was more effective than 5% ACV in altering the course of lesion development. While ACV significantly affected lesion development compared to placebo-treated animals, the effect was considerably less than observed for FIAU treated animals.

In animals inoculated with the ACV-resistant strain of HSV-2 (12247), all three concentrations of FIAU significantly reduced lesion scores and to a greater extent than ACV treatment, which was barely significant.

The effect of topical treatment with the FIAC preparations on lesion development is shown in TABLE VI. While both FIAC and ACV preparations significantly altered lesion development in animals inoculated with the ACV-sensitive MS strain, therapy with 5% or 1% FIAC reduced lesion scores to much lower levels than treatment with 5% ACV.

In animals infected with the ACV-resistant 12247 strain, again, therapy with 5% or 1% FIAC or with 5% ACV significantly reduced lesion development. However, treatment with 5% FIAC lowered lesion scores to a greater extent than 1% FIAC or 5% ACV.

TABLE II

EFFECT OF TOPICAL TREATMENT WITH FIAU ON VAGINAL VIRUS TITERS OF GUINEA PIGS INOCULATED INTRAVAGINALLY WITH HSV-2 STRAINS

| Treatment[a] | # Virus Positive/ # Inoculated | Virus Titer-Day Area Under Curve | P-Value | Mean Peak Virus Titer | P-Value |
|---|---|---|---|---|---|
| HSV-2, MS[b] | | | | | |
| Placebo-PBS | 10/10 | 31.8 | — | 5.0 | — |
| Placebo-Ointment | 10/10 | 32.8 | NS[c] | 5.3 | NS |
| FIAU 10% | 10/10 | 8.1 | 0.001 | 4.1 | <0.05 |
| FIAU 5% | 10/10 | 12.1 | <0.01 | 4.2 | <0.01 |
| FIAU 1% | 10/10 | 21.5 | 0.07 | 4.8 | NS |
| ACV 5% | 10/10 | 13.7 | <0.01 | 4.3 | <0.01 |
| HSV-2, 12247[d] | | | | | |
| Placebo-PBS | 10/10 | 33.5 | — | 4.8 | — |
| Placebo-Ointment | 10/10 | 34.4 | NS | 5.3 | NS |
| FIAU 10% | 9/9 | 20.5 | <0.05 | 4.6 | 0.01 |
| FIAU 5% | 10/10 | 21.8 | <0.05 | 4.2 | 0.001 |
| FIAU 1% | 10/10 | 31.7 | NS | 5.1 | NS |
| ACV 5% | 10/10 | 33.2 | NS | 4.8 | <0.05 |

[a]Topical and i.vag. treatment was initiated 24th after viral inoculation and was continued three times daily for 6 days.
[b]ACV sensitive strain of HSV-2, TK positive.
[c]NS = Not Statistically Significant when compared to the appropriate control or placebo-treated group.
[d]ACV resistant strain of HSV-2, TK altered.

TABLE III

EFFECT OF TOPICAL TREATMENT WITH FIAC ON VAGINAL VIRUS TITERS OF GUINEA PIGS INOCULATED INTRAVAGINALLY WITH HSV-2 STRAINS

| Treatment[a] | # Virus Positive/ # Inoculated | Virus Titer-Day Area Under Curve | P-Value | Mean Peak Virus Titer | P-Value |
|---|---|---|---|---|---|
| HSV-2, MS[b] | | | | | |
| Placebo-Ointment | 10/10 | 31.6 | — | 4.9 | — |
| FIAC 5% | 10/10 | 13.4 | <0.01 | 4.6 | NS[c] |
| FIAC 1% | 10/10 | 25.2 | NS | 4.5 | NS |
| ACV 5% | 10/10 | 14.2 | <0.01 | 4.5 | <0.05 |
| HSV-2, 12247[d] | | | | | |
| Placebo-Ointment | 10/10 | 34.4 | — | 4.8 | — |
| FIAC 5% | 10/10 | 21.3 | 0.01 | 4.2 | <0.01 |
| FIAC 1% | 10/10 | 32.9 | NS | 4.8 | NS |
| ACV 5% | 10/10 | 33.6 | NS | 4.8 | NS |

[a]Topical and i.vag. treatment was initiated 24th after viral inoculation and was continued three times daily for 6 days.
[b]ACV sensitive strain of HSV-2, TK positive.
[c]NS = Not Statistically Significant when compared to the appropriate control or placebo-treated group.
[d]ACV resistant strain of HSV-2, TK altered.

TABLE IV

EFFECT OF TOPICAL TREATMENT WITH FIAU ON EXTERNAL LESION DEVELOPMENT IN GENITAL HSV-2 INFECTIONS OF GUINEA PIGS

| Treatment[a] | Lesion Score- Day Area Under Curve | P-value | Mean Peak Lesion Score | P-Value |
|---|---|---|---|---|
| HSV-2, MS[b] | | | | |
| Placebo-PBS | 56.4 | — | 4.2 | — |
| Placebo-Ointment | 60.2 | NS[c] | 4.3 | NS |
| FIAU 10% | 0.5 | <0.001 | 0.3 | <0.001 |
| FIAU 5% | 1.0 | <0.001 | 0.5 | <0.001 |
| FIAU 1% | 2.0 | <0.001 | 0.8 | <0.001 |
| ACV 5% | 23.8 | <0.001 | 2.6 | 0.001 |
| HSV-2, 12247[d] | | | | |
| Placebo-PBS | 47.7 | — | 3.1 | — |
| Placebo-Ointment | 48.4 | NS | 3.2 | NS |
| FIAU 10% | 2.4 | <0.001 | 0.8 | <0.001 |
| FIAU 5% | 1.6 | <0.001 | 0.7 | <0.001 |
| FIAU 1% | 31.8 | 0.01 | 2.9 | NS |
| ACV 5% | 37.1 | 0.05 | 3.4 | NS |

[a]Topical and i.vag. treatment was initiated 24th after viral inoculation and was continued three times daily for 6 days.
[b]ACV sensitive strain of HSV-2, TK positive.
[c]NS = Not Statistically Significant when compared to the appropriate control or placebo-treated group.
[d]ACV resistant strain of HSV-2, TK altered.

TABLE V

EFFECT OF TOPICAL TREATMENT WITH FIAC ON EXTERNAL LESION DEVELOPMENT IN GENITAL HSV-2 INFECTIONS OF GUINEA PIGS

| Treatment[a] | Lesion Score- Day Area Under Curve | P-value | Mean Peak Lesion Score | P-Value |
|---|---|---|---|---|
| HSV-2, MS[b] | | | | |
| Placebo-Ointment | 37.5 | — | 3.7 | — |
| FIAC 5% | 1.4 | <0.001 | 0.4 | <0.001 |
| FIAC 1% | 6.5 | <0.001 | 1.1 | <0.001 |
| ACV 5% | 18.0 | <0.001 | 2.3 | 0.01 |
| HSV-2, 12247[c] | | | | |
| Placebo-Ointment | 42.1 | — | 2.6 | — |
| FIAC 5% | 2.4 | <0.001 | 0.8 | <0.001 |
| FIAC 1% | 20.8 | <0.01 | 2.7 | NS[d] |
| ACV 5% | 20.7 | <0.001 | 2.5 | NS |

[a]Topical and i.vag. treatment was initiated 24th after viral inoculation and was continued three times daily for 6 days.
[b]ACV sensitive strain of HSV-2, TK positive.
[c]ACV resistant strain of HSV-2, TK altered.
[d]NS = Not Statistically Significant when compared to the appropriate control or placebo-treated group.

It should be apparent to those skilled in the art that other compositions not specifically disclosed in the instant specification are, nevertheless, contemplated thereby. Such other compositions are considered to be within the scope and spirit of the present invention. Hence, the invention should not be limited by the description of the specific embodiments disclosed herein but only by the following claims.

What is claimed:

1. A method for treatment of infection or disease caused by a herpes virus strain that is resistant to treatment with acyclovir, which comprises administering to a subject in need of such treatment a composition which comprises an admixture of a pharmaceutically acceptable carrier with a compound of 1-(2'-deoxy-2'-fluoro-β-D-arabinofuranosyl)-5-iodouracil (FIAU), 1-(2'-deoxy-2'-fluoro-β-D- arabinofuranosyl)-5-iodocytosine (FIAC), 1-(2'-deoxy-2'-fluoro-β-D-arabinofuranosyl)uracil (FAU), 1-(2'-deoxy-2'-fluoro-β-D-arabinofuranosyl)-5-methyluracil (FMAU), or 1-(2'-deoxy-2'-fluoro-β-D-arabinofuranosyl)-5-ethyluracil (FEAU), in an amount sufficient to provide an antivirally effective dosage of said compound in the range of about 0.05 to about 10 mg/kg-day, a steady state peak plasma concentration of said compound in the range of about 0.1 to about 1 μg/ml, or about 0.1, 0.25, 0.5, 1, 5, 10 or 50 mg of said compound.

2. The method of claim 1 in which said composition is administered orally.

3. The method of claim 1 in which said composition is administered parenterally.

4. The method of claim 1 in which said composition is administered topically.

5. The method of claim 1 in which said treatment includes one or more administrations of said composition per day for a treatment period of about 7 to about 28 consecutive days.

6. The method of claim 5 in which said treatment period is about 14 consecutive days.

7. A method for topical treatment of infection or disease caused by a herpes virus strain that is resistant to treatment with acyclovir, which comprises administering to a subject in need of such treatment a composition which comprises a compound of 1-(2'-deoxy-2'-fluoro-β-D-arabinofuranosyl)-5-iodouracil (FIAU), 1-(2'-deoxy-2'-fluoro-β-D-arabinofuranosyl)-5-iodocytosine (FIAC), 1-(2'-deoxy-2'-fluoro-β-D-arabinofuranosyl)uracil (FAU), 1-(2'-deoxy-2'-fluoro-β-D-arabinofuranosyl)-5-methyluracil (FMAU), or 1-(2'-deoxy-2'-fluoro-β-D-arabinofuranosyl)-5-ethyluracil (FEAU) in an amount sufficient to provide a topical antivirally effective dosage of said compound in the range of about 0.05 to about 10 mg/kg-day, and a pharmaceutically acceptable carrier.

8. The method of claim 7 in which said infection or disease is topical.

9. The method of claim 7 in which said infection or disease is vaginal.

10. The method of claim 7 in which said infection or disease is ophthalmic.

11. The method of claim 7 in which said treatment includes one or more administrations of said composition per day for a treatment period of about 3 to about 30 consecutive days.

12. The method of claim 11 in which said treatment period is about 7, 14 or 21 consecutive days.

13. A method for topical treatment of infection or disease caused by a herpes virus strain that is resistant to treatment with acyclovir, which comprises administering to a subject in need of such treatment a composition which comprises a concentration of a compound of 1-(2'-deoxy-2'-fluoro-β-D-arabinofuranosyl)-5-iodouracil (FIAU), 1-(2'-deoxy-2'-fluoro-β-D-arabinofuranosyl)-5-iodocytosine (FIAC), 1-(2'-deoxy-2'-fluoro-β-D-arabinofuranosyl)uracil (FAU), 1-(2'-deoxy-2'-fluoro-β-D-arabinofuranosyl)-5-methyluracil (FMAU), or 1-(2'-deoxy-2'-fluoro-β-D-arabinofuranosyl)-5-ethyluracil (FEAU) which concentration if tested in an in vitro plaque reduction assay is equivalent to 20 percent or greater of the concentration of said compound (in μg/ml) required to reduce the plaque formation induced by said herpes virus strain by fifty percent ($EC_{50}$), and a pharmaceutically acceptable carrier.

14. The method of claim 13 in which said infection or disease is topical.

15. The method of claim 13 in which said infection or disease is vaginal.

16. The method of claim 13 in which said infection or disease is ophthalmic.

17. The method of claim 13 in which said treatment includes one or more administrations of said composition per day for a treatment period of about 3 to about 30 consecutive days.

18. The method of claim 17 in which said treatment period is about 7, 14 or 21 consecutive days.

19. A method for topical treatment of infection or disease caused by a herpes virus strain that is resistant to treatment with acyclovir, which comprises administering to a subject in need of such treatment a composition which comprises a compound of 1-(2'-deoxy-2'-fluoro-β-D-arabinofuranosyl)-5-iodouracil (FIAU), 1-(2'-deoxy-2'-fluoro-β-D-arabinofuranosyl)-5-iodocytosine (FIAC), 1-(2'-deoxy-2'-fluoro-β-D-arabinofuranosyl)uracil (FAU), 1-(2'-deoxy-2'-fluoro-β-D-arabinofuranosyl)-5-methyluracil (FMAU), and 1-(2'-deoxy-2'-fluoro-β-D-arabinofuranosyl)-5-ethyluracil (FEAU) or a pharmaceutically acceptable carrier, said composition containing about 0.1–25 percent (w/w) of said compound.

20. The method of claim 1, 7, 13, or 19, wherein the herpes virus strain that is resistant to treatment with acyclovir is selected from the group consisting of HSV-1 virus strains SC 16-S1, DM 2.1, 11893, 11359, 11360, and B-2006 and HSV-2 virus strains 8707, 8711, 12247, 11680, 11575, 11572, 11361, AG-3, and 11785.

21. The method of claim 7, 13, or 19, wherein the herpes virus strain that is resistant to treatment with acyclovir is an HSV-2 virus strain and said compound is 1-(2'-deoxy-2'-fluoro-β-D-arabinofuranosyl)-5-iodouracil (FIAU) or 1-(2'-deoxy-2'-fluoro-β-D-arabinofuranosyl)-5-iodocytosine (FIAC).

22. The method of claim 19 in which said infection or disease is topical.

23. The method of claim 19 in which said infection or disease is vaginal.

24. The method of claim 19 in which said infection or disease is ophthalmic.

25. The method of claim 19 in which said treatment includes one or more administrations of said composition per day for a treatment period of about 3 to about 30 consecutive days.

26. The method of claim 25 in which said treatment period is about 7, 14 or 21 consecutive days.

27. The method of claim 21, wherein said HSV-2 virus strain is 12247 or AG-3.

* * * * *